United States Patent [19]

Happel et al.

[11] 4,151,191
[45] Apr. 24, 1979

[54] SULFUR RESISTANT MOLYBDENUM CATALYSTS FOR METHANATION

[75] Inventors: John Happel, Hastings-on-Hudson, N.Y.; Miguel A. Hnatow, Verona, N.J.

[73] Assignee: The American Gas Association, Arlington, Va.

[21] Appl. No.: 851,556

[22] Filed: Nov. 14, 1977

[51] Int. Cl.$^2$ ............................................. C07C 27/06
[52] U.S. Cl. ........................... 260/449 M; 48/197 R; 252/439; 252/462; 252/465; 252/467; 260/449.6 M
[58] Field of Search ........................ 48/197 R, 214 A; 260/449 M, 449.6 M; 252/439, 462, 465, 467

[56] References Cited

U.S. PATENT DOCUMENTS

| | | | |
|---|---|---|---|
| 3,099,617 | 7/1963 | Tulleners | 252/439 |
| 3,642,460 | 2/1972 | Thompson | 260/449 M |
| 3,839,225 | 10/1974 | Acres | 48/214 A |
| 3,927,997 | 12/1975 | Child et al. | 260/449 M |
| 3,988,263 | 10/1976 | Hansford | 260/449 M |
| 4,060,498 | 11/1977 | Kawagoshi et al. | 48/214 A |

*Primary Examiner*—S. Leon Bashore
*Assistant Examiner*—George C. Yeung
*Attorney, Agent, or Firm*—E. Janet Berry; Lawrence Rosen

[57] ABSTRACT

A process for the production of methane or methane containing gas from a feed mixture containing hydrogen, carbon monoxide, and gaseous compounds of sulfur, by contacting said feed mixture with a solid catalyst having from 1% up to 99% by weight of molybdenum and from 99% to 1% by weight of at least one element of the lanthanide or actinide groups of elements or mixtures thereof, at a temperature of from about 300° C. to 600° C. and a pressure of from about 100 psig. to 2000 psig.

7 Claims, No Drawings

SULFUR RESISTANT MOLYBDENUM CATALYSTS FOR METHANATION

There has been discovered a methanation process for making fuel gas containing enhanced amounts of methane using a sulfur resistant molybdenum containing catalyst together with at least one element from the lanthanide or actinide groups of elements and gas feed streams containing substantial amounts of sulfur containing compounds.

It is an object of the invention to provide an improved methanation process employing a molybdenum containing catalyst.

It is another object of the invention to prepare methane from mixtures of carbon monoxide and hydrogen containing sulfur containing compounds.

Another object is to use molybdenum containing catalyst to produce gas products having a high content of methane as well as other gaseous products.

It is well known that there exists at the present time a critical shortage of natural gas. In the past a number of processes have been developed to produce synthesis gas which is a mixture of carbon monoxide and hydrogen, from fossil fuels including coal and petroleum hydrocarbons. All these synthetic processes ultimately require the step of hydrogenation of carbon monoxide to produce methane. The process by which this conversion is accomplished is generally described as methanation. All presently used commercial processes employ for this final step catalysts containing nickel supported on various materials. It is well-known, however, that nickel is very sensitive to poisoning by any sulfur containing compounds present in the feed gas. It has therefore been found necessary to maintain the sulfur content of such synthesis gas streams to below 0.1 parts per million (ppm) in order to avoid rapid deterioration of the nickel catalysts. Removal of sulfur to such low concentrations is very costly, requiring not only the usual extraction or absorption by alkaline media such as the ethanolamines, but actual chemical reaction of the sulfur with ZnO to produce ZnS.

In recent comprehensive review of methanation by Mills and Steffgen, "Catalytic Methanation", Catalysis Reviews 8 (2), 159–210 (1973) the activity of molybdenum and tungsten compounds for methanation in the presence of sulfur containing gases is discussed. Sulfur resistant catalysts for hydrodesulfurization consisting of combinations of cobalt/nickel/alumina/molybdenum/-tungsten oxide combinations have been used in the past for catalytic refining of high sulfur petroleum stocks. In a recent patent issued to Child et al., U.S. Pat. No. 3,928,000, the use of such a sulfur resistant catalyst having the composition of parts by weight of CoO 3.2, $MoO_3$ 15.7 and $Al_2O_3$ 81.1 for methanation of $H_2/CO$ mixtures containing $H_2S$ is disclosed. Similar catalyst containing nickel and tungsten are also disclosed in this patent. It has now been discovered that the use of lanthanide and/or actinide oxides substantially improves the performance of molybdenum containing catalyst for methanation in the presence of sulfur compounds.

The molybdenum based catalysts which have been found to give outstanding results operate with moderate amounts of methane produced by the reaction:

$$CO + 3H_2 = CH_4 + H_2O \qquad (1)$$

They also form $CO_2$ according to the overall reaction (2), the water gas shift reaction:

$$CO + H_2O = CO_2 + H_2 \qquad (2)$$

The sum of reactions (1) and (2) constitutes a third possible route for simultaneous methane and $CO_2$ production:

$$2CO + 2H_2 = CH_4 + CO_2 \qquad (3)$$

It is not known whether reaction (3) occurs independently or substantially as a result of the combination of reactions (1) and (2) but the formation of $H_2$ by reaction (2) obviates the necessity for operating at hydrogen to CO ratios of 3/1 which ratios are necessary if the methanation catalyst used only promotes Reaction (1) as is the case with nickel.

As in the case of earlier investigations by others, it has been found that molybdenum oxides in combination with aluminum oxide alone and when used with both aluminum and cobalt oxides exhibit methanation activity in the presence of sulfur-containing synthesis gas. Additionally we have discovered unexpectedly that elements from the rare earth and actinide groups of the periodic table impart useful catalytic properties to molybdenum formulation.

Synthesis gas may be produced from a variety of hydrocarbonaceous fuels with sulfur contents in the range of 1 to 7 wt. %. Suitable feed stocks to gas generating equipment may include various petroleum distillates and residue, asphalt, coal tar, coal oil, petroleum coke, coal, tar sands, shale oil, char, coke, particulate carbons and the like. To convert a heavy hydrocarbon of a carbon to hydrogen stream ratio of 1:2 or higher to methane, which has a C/H ratio of 1:4 it is necessary to either introduce hydrogen in gaseous form or generate hydrogen within the system from steam.

The high degree of exothermicity of the methanation reaction and the fact that at high temperatures the methanation equilibrium reaction shifts toward the carbon monoxide/hydrogen side makes it necessary to cool the reaction either internally or externally. For example, the methanation can be carried out in an inert liquid which is simultaneously cooled to maintain constant temperature. An alternative approach is the use of a fluid bed of catalyst which permits simultaneous reaction and cooling of the reacting gases. With fixed bed reactors temperature control may be achieved by means of separate inlet points, embedding tubular coolers in the catalyst beds and producing steam which may be used elsewhere in the process, and cooling the effluent gas between beds with simultaneous steam generation. The gas temperature may also be controlled by using a free flow tubular reactor where inside surfaces are coated with catalyst. Another method of controlling catalyst bed temperature consists of recycling a portion of the product gases through the catalyst bed in admixture with fresh feed gas at ratios ranging from 2.5 to 50 volumes of recycle gas per volume of fresh feed gas and preferably recycle ratios in the range of 1 to 8.

The sulfur resistant catalyst containing molybdenum oxide disclosed herein may be used alone supported on a structure formed of such materials as diatomaceous earth, alumina, silica stabilized alumina, magnesium silicate, magnesium aluminate, magnesia, barium sulfate, magnesium titanate, and the like.

The operating conditions in a fixed bed sulfur resistant catalytic methanator are entrance temperature in the range of about 300° to 600° C. and exit temperatures in the range of 300° to 850° C. and preferably in the range of about 400° to 700° C., pressure in the range of about 1 to 250 atmospheres and preferably equal to that required to enter a pipeline system or up to about 65 atm, and a space velocity in the range of about 80 to 10,000 standard volumes of gas per volume of catalyst per hour (v/v/hr).

Alternatively in a fluidized bed methanator the sulfur resistant catalyst has a preferred particle size of 20 to 1000 microns. Operating conditions include temperatures in the range of about 300° to 800° C. and preferably 400° to 700° C., pressure 1 to 65 atmospheres and contact time 0.5 to 10 seconds.

The effluent gas stream from the sulfur resistant catalytic methanator has the following analysis in mole %: $CH_4$, 5 to 95; CO nil to 45; $H_2$ nil to 50; $CO_2$ nil to 50; $H_2O$ nil to 50; $H_2S$ nil to 3; COS nil to 2.0 and $Ar+N_2$ nil to 5.0.

The effluent gas stream from the sulfur resistant catalytic methanator is cooled, for example, in a waste heat boiler. By this means water is converted into steam, and the temperature of the gas stream is reduced to 120°–350° C. The steam may be used elsewhere as may be required in the system.

In the next step, $CO_2$, $H_2O$, $H_2S$ COS and $AR+N_2$ are removed from the process stream in a gas purification zone. This may be done by suitable conventional processing involving cooling and physical or chemical absorption by solvents, such as methyl alcohol, n-methyl pyrrolidone, triethanolamine, propylene carbonate, and potassium carbonate. Preferably methane is substantially insoluable in the solvent used. Most of the $CO_2$ absorbed in the solvent can often be released by flashing. The stream of $CO_2$ may be used for organic synthesis. Optionally, a portion of the $CO_2$ stream may be introduced into the gas generator as a modifier for the reaction. The regenerated solvent is recycled to the absorption column for reuse.

$H_2S$ and COS-containing solvent is regenerated by further flashing or stripping. The $H_2S$ and COS may then be converted to sulfur, for example by such processes as the known Claus process.

The substantially dry gaseous mixture from the gas purification zone has the following composition in mole percent: $H_2$, 0 to 50; CO, 0 to 50; $CH_4$, 10 to 95; $CO_2$, 0 to less than 1; $Ar+N_2$, 0 to 1.0; and 0 to less than about 0.3 parts per million of total sulfur, i.e., $H_2S+COS$. Its gross heating value is in the range of about 350 to 950 Btu per SCF. This gas may be used as a fuel gas.

Optionally, to prepare substantially pure methane, the gas stream may be further processed by several methods. Sufficient water could be added to the stream and it could be reacted in a conventional water gas shift reaction system to convert CO to $CO_2$ and $H_2$. The $H_2$ would react with CO in a polishing methanation reactor to further reduce both $H_2$ and CO. Alternatively CO could be removed by the use of solvent systems designed to extract CO from gas streams.

This process shows the following specific advantages for making fuel gas:

a. The initial methanation, and the most difficult one to control, can be undertaken without necessity for preliminary water gas shift to increase the ratio of $H_2/CO$ in the feed gas to the methanation. Usually this step is necessary with the conventional nickel catalyst since all nickel containing catalysts are poisoned by sulfur.

b. The gases from the syn gas generator do not have to be cooled down before methanation to remove $H_2S$.

c. The high energy released in the process is at a high temperature so that it can be recovered at a higher thermal efficiency. Thus, by-product steam may be produced at higher temperatures.

d. A clean fuel gas is produced which may be used universally without polluting the atmosphere.

e. The product gas may be used interchangeably with natural gas and may be transported in the same pipeline.

f. The product gas may be produced substantially at pipeline pressure, thus eliminating costly compressors.

In addition, as compared with the usual methanation process, substantial economies can be effected, in that the steps of water gas shift and methanation could be combined and thus the expensive sulfur removal equipment eliminated.

The following examples present the experimental data obtained under typical operating conditions using the molybdenum containing catalysts and are presented as embodiments of the invention. It is, however, not intended to limit the invention or its scope in any way thereto. All catalyst compositions are by weight unless otherwise specified.

EXAMPLE 1

Methanation of a mixture of carbon monoxide and hydrogen was carried out by passing a mixture of the gases upwardly through a fixed bed reaction consisting of a stainless steel tube 1" in diameter and 14" in length. The feed gas mixture was preheated by a resistance heater surrounding the tube. Two additional resistance heaters were employed to control temperature in the reactor. Pressure was controlled by a needle valve in the exit stream. Exit gases were analyzed by an F and M Lab Chromatograph Model 700 equipped with a temperature programmer. The components analyzed for included CO, $CO_2$, $CH_4$, $H_2O$, $H_2S$, $C_2H_2$, $C_2H_4$, $C_2H_6$, $N_2$ and $H_2$.

The catalyst employed in this Example contained the cations lanthanum and cobalt supported on alumina. It was prepared as follows:

86.6 gm $La(NO_3)_3.6H_2O$ and 58.2 gm of $Co(NO_3)_2$ $6H_2O$ were dissolved in 20 gm of distilled water. 111 gm of $Al_2O_3$ were added to the solution. The solution was dried to a powder in an oven at 110° C. for 16 hrs. and calcined at 538° C. for 1 hr. 5 cc of the resulting catalyst powder was charged to the reactor.

A mixture consisting of 25%-vol CO and 75%-vol $H_2$ and containing 2000 ppm (parts per million) of $H_2S$ was passed over the catalyst at a space velocity of 4800 v/v/hr (standard temperature and pressure), a temperature of about 500° C. and a pressure of 200 lbs/sq. in. gauge (psig).

Under these reaction conditions, a total of 12.4% of the CO present in the feed was converted. The selectivity to $CH_4$ was 40%. That is 40% of the CO converted reacted to produce $CH_4$. Thus a once through yield of 4.9% of the feed CO was converted to methane. The remaining 7.5% of the CO was converted to $CO_2$ with concomitant hydrogen production.

EXAMPLE 2

The same apparatus and procedure as employed in Example 1 were used to test the activity of a catalyst based on lanthanum, molybdenum and cobalt oxides.

The catalyst employed was prepared as follows:

65 grams of $La(NO_3)_3.6H_2O$, 26.8 gm of $(NH_4)_6 Mo_7O_{24}.4H_2O$ and 14.5 gm of $Co(NO_3)_2.6H_2O$ were added to 25 cc of distilled water. 140 gm of $Al_2O_3$ were added to the solution. The slurry was then dried in an oven at 110° C. for 16 hrs. and calcined at 538° C. for 1 hour. 5 cc of the resulting catalyst was charged to the described reactor.

A mixture consisting of 25 vol % CO and 75 vol % $H_2$ was passed through the catalyst bed at a space velocity of 4800 v/v/hr (STP), 500° C. and a pressure of 200 psig. A conversion of 23.6% of the inlet CO was obtained at a selectivity to methane of 56%. Thus the once-through methane yield from the CO feed was 13.2%. This is substantially higher than that obtained using lanthanum and cobalt oxides as described in Example 1.

EXAMPLE 3

The same apparatus and procedure as that employed in Example 1 were used to test the activity of a catalyst consisting of only lanthanum and molybdenum compounds without the presence of cobalt. The catalyst employed was prepared as follows:

34.3 grams of $La(NO_3)_3.6H_2O$ and 21 grams $(NH_4)_6 Mo_7O_{24}.4H_2O$ were added to 25 cc of distilled water. To the mixture 96 grams of $Al_2O_3$ were added. The slurry was then dried in an oven at 110° C. for 16 hours and calcined at 538° C. for 1 hour. 5 cc of the resulting catalyst was charged to the described reactor.

A mixture consisting of 25 vol % of CO and 75 vol % of $H_2$ and containing 400 ppm of $H_2S$ was passed through the catalyst bed at a space velocity of 4800 v/v/hr (STP), a temperature of 500° C. and a pressure of 200 psig. A conversion of 25.2% of the CO present in the feed gas was obtained at a selectivity to methane of 58%. Thus, the once-through methane yield from the CO feed was 14.6%. Comparison with Example 2 indicates that the lanthanum rather than the cobalt is responsible for the improved performance of this catalyst.

EXAMPLE 4

The same apparatus and procedure as that employed in Example 1 were used to test the activity of a catalyst containing a relatively high La/Mo atomic ratio of 9/1. The catalyst employed was prepared as follows:

80.0 gm of $La(NO_3)_3.6H_2O$ and 3.6 gm of $(NH_4)_6 Mo_7O_{24}.4H_2O$ were added to 20 cc of distilled water. The solution was heated over a bunsen burner flame until a thick slurry was formed. The slurry was dried in an oven at 110° C. for 16 hours and calcined at 538° C. for 1 hour. 5 cc of the resulting catalyst powder was charged to the reactor.

A mixture consisting of 25 vol % of CO and 75 vol % of $H_2$ containing 2000 ppm of $H_2S$ was passed through the catalyst bed at a space velocity of 4800 v/v/hr (STP), a temperature of 500° C. and a pressure of 200 psig. Under these conditions a CO conversion of 5.4% was obtained at a selectivity of 55% to $CH_4$, corresponding to a once-through yield of 2.97% methane. This indicates that higher proportions of lanthanum are not as effective in enhancing the methanation catalyst activity in La/Mo combinations.

EXAMPLE 5

The same apparatus and procedure as that employed in Example 1 were used to test the activity of a catalyst containing a relatively high Ce/Mo atomic ratio of 9/1. The catalyst employed was prepared as follows:

43.4 gm of $Ce(NO_3)_3.6H_2O$ and 1.95 gm of $(NH_4)_6 Mo_7O_{24}.4H_2O$ were dissolved in 20 cc of distilled water. The solution was heated over a bunsen burner flame until thick slurry was formed. The slurry was dried in an oven at 110° C. for 16 hrs. and calcined in 538° C. for 1 hour. The catalyst was pressed to a cake (20,000 psi). The cake was cracked and sieved to a size between 6 and 8 mesh. 5 cc of this catalyst was charged to the reactor.

A mixture consisting of 25 vol % of CO and 75 vol % of $H_2$ containing 2000 ppm of $H_2S$ was passed through the catalyst bed at a space velocity of 4800 v/v/hr (STP), a temperature of 450° C. and a pressure of 200 psig.

Under these conditions a conversion of CO of 40.1 was obtained with a selectivity to methane of 50%, corresponding to 20.0% yield of $CH_4$ on a once-through basis from the feed stream CO content. This is substantially better than the result obtained with lanthanum.

EXAMPLE 6

The same apparatus and procedure as that employed in Example 1 were used to test the activity of a catalyst consisting of pure $CeO_2$. The catalyst employed was prepared as follows:

78 gm of $Ce(NO_3)_3.6H_2O$ were dissolved in 25 cc of distilled water. The solution was heated over a bunsen burner flame until a thick slurry was formed. The slurry was dried in an oven at 110° C. for 16 hr. and then calcined at 538° C. for 1 hour. The catalyst was pressed to a cake (20,000 psi). The cake was cracked and sieved to a size between 6 and 8 mesh. 5 cc of this catalyst were charged to the reactor.

A mixture consisting of 25 vol % of CO and 75 vol % of $H_2$ and containing 2000 ppm of $H_2S$ was passed over the catalyst at a temperature of 450° C. and a pressure of 200 psig. Under these conditions a conversion of CO of 29.2% was obtained. The selectivity of $CH_4$ was 52%, corresponding to an overall yield of $CH_4$ on a once-through basis of 15.2%. While high, this is a substantially poorer result than that obtained by the addition of a small proportion of molybdenum as shown in Example 4.

EXAMPLE 7

An apparatus the same as that employed in Example 1 was used to test the activity of a catalyst in which the actinide $UO_2$ was used in a molybdenum catalyst formulation. The catalyst was prepared as follows:

23.8 gm of $UO_2(C_2H_3O_2)_2.2H_2O$ and 1.76 gm of $(NH_4)_6 Mo_7O_{24}.4H_2O$ were added to 25 cc of distilled water. The resulting solution was heated over a bunsen burner flame until a thick slurry was formed. The slurry was dried in an oven at 110° C. for 16 hours and calcined at 538° C. for 1 hour. The resulting catalyst was compressed to a cake (20,000 psi). The cake was cracked and sieved to a size between 6 and 8 mesh. 5 cc of this catalyst was charged to the reactor.

A mixture consisting of 25 vol % of CO and 75 vol % of $H_2$ and containing 400 ppm of $H_2S$ was passed over the catalyst at a temperature of 450° C. and a pressure of 200 psig. The conversion of CO in the feed corresponded to 14.0% with a selectivity to $CH_4$ of 62%. Thus a once-through conversion of the CO in the feed of 8.7% was obtained.

EXAMPLE 8

An apparatus the same as that employed in Example 1 was used to test the activity of a catalyst in which the actinide $ThO_2$ was used in a molybdenum catalyst formulation. The catalyst was prepared as follows:

55.2 gm of $Th(NO_3)_4.4H_2O$ and 1.95 gm $(NH_4)_6Mo_7O_{24}.4H_2O$ were added to 20 cc of distilled water. The solution was heated over a bunsen burner flame until a thick slurry was formed. The slurry was dried in an oven at 110° C. for 16 hours and calcined at 538° C. for 1 hour. The resulting catalyst was compressed to a cake (20,000 psi). The cake was cracked and sieved to a size between 6 and 8 mesh. 5 cc of this catalyst were charged to the reactor.

A mixture consisting of 25 vol % of CO and 74 vol % of $H_2$ was passed through the bed at a space velocity of 4800 v/v/hr (STP), 475° C. and 200 psig. Under these conditions using a feed gas containing 400 ppm of $H_2S$, a conversion of 32.1% of the CO present in the feed was converted with a selectivity of 57% conversion to $CH_4$. This corresponds to a once-through yield of $CH_4$ based on CO in the feed of 18.3%.

EXAMPLE 9

An apparatus the same as that employed in Example 1 was used to test the activity of a catalyst in which $Al_2O_3$ was used in a molybdenum catalyst formulation. The catalyst was prepared as follows:

13.94 gm of molydbic acid (86.1% $MoO_3$) were slurried in a solution made by dissolving 58.8 gm of $Al(NO_3)_3.9H_2O$ in 20 cc of distilled water. The solution was heated over a bunsen burner flame until a thick slurry was formed. The slurry was dried at 110° C. for 16 hours, calcined at 538° C. for 1 hour. The catalyst was compressed to a cake (20,000 psi). The cake was cracked and sieved to a size between 6 and 8 mesh. 5 cc of this catalyst was charged to the reactor.

A mixture consisting of 25 vol % of CO and 75 vol % of $H_2$ containing 400 ppm of $H_2S$ was passed through the bed at a space velocity of 4800 v/v/hr (STP), at a temperature of 475° C. and a pressure of 200 psig. A conversion of CO of 25.6% was obtained at a selectivity of 58% to $CH_4$ corresponding to a once-through yield of 14.85% of $CH_4$ based on the CO in the feed. Thus, although several times as much molybdenum was present in the alumina based catalyst, the yield was somewhat less than that when using thoria as in Example 8.

EXAMPLE 10

An apparatus the same as that employed in Example 1 was used to test the activity of a catalyst in which Ce/Mo catalyst was employed under high pressure conditions. The catalyst was prepared as described under Example 5. 5 cc of this catalyst was charged to the reactor.

Feed gases with those ratios of $H_2/CO$ were passed over the catalyst, namely $H_2/CO = 3/1$, 2/1 and 1/1. All feed gases contained 2500 ppm of $H_2S$. The space velocity employed was 4800 v/v/hr (STP) at a temperature of 500° C. Several pressures were employed. Results are summarized in Table 1.

| Feed RAtio $H_2/CO$ | Pressure psig | CO conversion % | $CH_4$ selectivity % | $CH_4$ yield % |
|---|---|---|---|---|
| 3/1 | 2200 | 55.1 | 63.0 | 34.7 |
| 3/1 | 500 | 78.8 | 61.5 | 48.5 |
| 3/1 | 1000 | 82.1 | 57.1 | 46.9 |
| 2/1 | 200 | 50.0 | 53.8 | 26.9 |
| 2/1 | 500 | 64.9 | 55.6 | 36.1 |
| 2/1 | 1000 | 77.0 | 59.5 | 45.8 |
| 1/1 | 200 | 45.3 | 51.4 | 23.3 |
| 1/1 | 500 | 53.5 | 49.3 | 26.4 |
| 1/1 | 1000 | 66.3 | 47.8 | 31.7 |

It can be concluded that, in general, higher pressures and higher $H_2/CO$ ratios favor higher conversions.

It has been found in many experiments of varied types that molybdenum containing catalysts enhance the conversion of CO to methane (methanation) and in many cases smaller amounts of higher hydrocarbons such as ethane are also produced. Operating conditions include temperatures in the range of 300°-550° C. About 400°-450° C. is the preferred temperature. At lower temperatures conversion is not as high. At sufficiently high temperatures the methane produced may be decomposed to carbon and hydrogen. A pressure range from 100-2000 lbs/sq. in gauge is feasible. At lower pressures yields are somewhat reduced. A pressure of 1000 psig is of interest because pipeline supply systems operate in this region and it is attractive economically to compress the feed gas before catalysis, rather than first conduct the catalytic operation at a lower pressure and then compress it. Pressures up to 2000 psig and higher, however, are useful since higher yields are obtained in accordance with Le Chatelier's principle that a reaction in which volume decreases such as Reaction 1 will be thermodynamically favored by higher pressures. Space velocities from 50-10,000 v/v/hr (at standard temperature and pressure) are useful. At lower space velocities the operation would not be economical. Higher space velocities result in lower conversions per pass. Space velocities in the range of 150-1000 v/v/hr are optimum for most reactions. These catalysts have the special advantage that they can perform effectively with feed gases containing up to 3 vol % and higher of gaseous compounds of sulfur in concentrations of up to 30,000 ppm. The gaseous mixture may contain hydrogen and carbon monoxide in a ratio of $H_2/CO = 5/1$ to 1/1.

As for catalyst composition, it is known that molybdenum can exist in several oxidation states. The useful catalytic properties of $MoO_3$ supported on silica or alumina are associated with a lower oxidation state, possibly $Mo^{+5}$. The solid state chemistry of the lower oxidation state of molybdenum is complicated. A number of non-stoichiometric oxides lying between $MoO_3$ and $MoO_2$ have been prepared and characterized. These oxidation states may well occur during the reaction of molybdenum oxides with synthesis gas mixtures.

Molybdenum sulfides are also numerous, the following having been discussed in the literature; $MoS_4$, $MoS_3$, $Mo_2S_5$, $MoS_2$ and $Mo_2S_3$. $MoS_2$ is the compound most easily prepared and in both sulfiding and reducing atmospheres in molybdenum oxides $MoO_3$ and $MoO_2$ as well as the higher molybdenum sulfides are converted at least partially to $MoS_2$. $MoS_2$ occurs in two different crystalline forms, hexagonal and rhombohedral.

It is believed that both molybdenum oxides in the range $MoO_{2-3}$ and sulfides in the range $MoS_{1.5-2}$ or mixtures of these materials are active methanation catalysts under the reaction conditions described herein.

The presence of alumina as an additional component has also not been well characterized. It is believed to perform a useful function in hydrodesulfurization catalysts and extensive study by Wencke (Freiberger Forschungsh. A151, 11–29 (1960)). indicates that a large proportion of alumina is necessary for highest activity, but pure alumina and $MoO_3$ are relatively less active. Sulfiding decreases the activity of molybdena-alumina catalysts for methanation. The role of alumina is believed to be that of dispersing the active component, molybdena. It is also considered that alumina may also prevent the molybdenum from being reduced to lower states of oxidation than +4.

Thus it has been discovered that rare earth and actinide group elements are more effective than aluminum in enhancing the catalytic activity of molybdenum containing catalysts for methanation. The addition of third components such as aluminum, tungsten and silicon may have further advantageous properties.

What is claimed is:

1. A process for producing methane, and other gaseous hydrocarbons from hydrogen and carbon monoxide by contacting a gaseous mixture containing hydrogen, carbon monoxide, and gaseous compounds of sulfur in concentrations of up to 30,000 ppm with a catalyst comprising oxygen compounds of an element selected from the group consisting of the lanthanide elements and the actinide elements and oxygen compounds of molybdenum, the atomic ratio of said elements to molybdenum being about 9 to 1.

2. A process for producing a methane containing gas from a gaseous mixture containing hydrogen and carbon monoxide in the ratio of $H_2/CO = 5/1$ to $1/1$, other gaseous components and gaseous compounds of sulfur in concentrations of up to 30,000 ppm by contacting said gaseous mixture at a temperature of from about 300° C. to about 600° C.; at a pressure of from 100 psig. to 2000 psig. and at a space velocity of from 80 to 10,000 v/v/hr (STP) with a catalyst comprising oxygen compounds of an element selected from the group consisting of the lanthanide elements and the actinide elements and oxygen compounds of molybdenum, the atomic ratio of said element to molybdenum being about 9 to 1.

3. A process for producing a gas containing methane according to claim 1 in which the catalyst comprises oxygen compounds of an element selected from the group consisting of La, Ce, Th, and U and oxygen compounds of molybdenum, the atomic ratio of said element to molybdenum being about 9 to 1.

4. A process for producing a gas containing methane according to claim 2 in which the catalyst contains oxygen compounds of an element selected from the group consisting of La, Ce, Th and U, and oxygen compounds of molybdenum, the atomic ratio of said element to molybdenum being about 9 to 1.

5. A process according to claim 1 in which the catalyst contains cerium oxides and molybdenum oxides, the atomic ratio of cerium to molybdenum being about 9 to 1.

6. A process according to claim 1 in which the catalyst consists of molybdenum and cerium oxides and additionally sulfides, the atomic ratio of cerium to molybdenum being about 9 to 1.

7. A process for producing a gas containing methane and other gaseous hydrocarbons from a mixture containing hydrogen and carbon monoxide according to claim 6.

* * * * *